United States Patent
Liu et al.

(10) Patent No.: US 8,412,310 B2
(45) Date of Patent: Apr. 2, 2013

(54) LOCKING SYRINGE WITH INTEGRATED BIAS MEMBER

(75) Inventors: Yunxing Liu, Maplewood, MN (US); Chun Li, BeiJing (CN)

(73) Assignee: United Medical Innovations, Inc., Maplewood, MN (US)

( * ) Notice: Subject to any disclaimer, the term of this patent is extended or adjusted under 35 U.S.C. 154(b) by 771 days.

(21) Appl. No.: 12/563,002

(22) Filed: Sep. 18, 2009

(65) Prior Publication Data
US 2011/0071393 A1    Mar. 24, 2011

(51) Int. Cl.
*A61M 5/315* (2006.01)
*A61M 5/00* (2006.01)

(52) U.S. Cl. ..... 600/432; 600/420; 600/421; 604/93.01; 604/131; 604/181; 604/187; 604/218

(58) Field of Classification Search ........... 600/420, 600/421, 432; 604/93.01, 131, 181, 187, 604/218
See application file for complete search history.

(56) References Cited

U.S. PATENT DOCUMENTS

| | | | |
|---|---|---|---|
| 2,309,502 A * | 1/1943 | Douglas | 604/135 |
| 2,413,303 A | 12/1946 | Folkman | |
| 3,880,163 A | 4/1975 | Ritterskamp | |
| 4,659,327 A * | 4/1987 | Bennett et al. | 604/135 |
| 4,668,220 A * | 5/1987 | Hawrylenko | 604/155 |
| 4,711,637 A | 12/1987 | Leigh et al. | |
| 4,755,172 A | 7/1988 | Baldwin | |
| 4,874,385 A | 10/1989 | Moran et al. | |
| 4,929,238 A * | 5/1990 | Baum | 604/208 |
| 4,966,585 A | 10/1990 | Gangemi | |
| 5,047,015 A | 9/1991 | Foote et al. | |
| 5,057,078 A | 10/1991 | Foote et al. | |
| 5,100,389 A | 3/1992 | Vaillancourt | |
| 5,160,327 A | 11/1992 | Stines | |
| 5,290,260 A | 3/1994 | Stines | |
| 5,318,534 A | 6/1994 | Williams et al. | |
| 5,429,607 A | 7/1995 | Mcphee | |
| 5,531,708 A | 7/1996 | Woodruff | |
| 5,579,767 A * | 12/1996 | Prince | 600/419 |
| 5,599,315 A | 2/1997 | Mcphee | |
| 5,733,261 A | 3/1998 | Obong | |
| 5,800,405 A | 9/1998 | Mcphee | |
| 6,019,747 A | 2/2000 | Mcphee | |
| 6,579,263 B1 | 6/2003 | Chernack | |
| 7,008,433 B2 | 3/2006 | Voellmicke et al. | |
| 7,111,757 B1 | 9/2006 | O'Brien et al. | |
| 2008/0033359 A1 | 2/2008 | Kazemzadeh | |
| 2009/0177156 A1 | 7/2009 | Maclean | |

* cited by examiner

FOREIGN PATENT DOCUMENTS

| | | |
|---|---|---|
| EP | 2027832 A2 | 2/2009 |
| WO | WO-03059415 A2 | 7/2003 |

*Primary Examiner* — Brian Casler
*Assistant Examiner* — Phong K Huynh
(74) *Attorney, Agent, or Firm* — Schwegman Lundberg Woessner P.A.

(57) ABSTRACT

A locking syringe with an integrated bias member, for delivering medical fluids at high pressure, can include a housing, a shaft, a piston, a cap assembly, a bias member, and a locking member. A distal end of the housing can interface with a patient delivery apparatus. A piston can be connected to the distal end of the shaft and can include a peripheral sealing surface that can slidably engage the inside surface of the housing to form a movable seal. The cap assembly at the proximal end of the housing can engage the shaft. A base cap can secure the piston within the housing. The bias member can have a distal end coupled to the piston and a proximal end restrained, such as to help pressurize the internal cavity. The user-actuatable locking member can user-selectively engage and inhibit unwanted movement of the shaft.

10 Claims, 5 Drawing Sheets

LOCKING SYRINGE WITH INTEGRATED BIAS MEMBER

BACKGROUND

Syringes are commonly used in many different medical procedures to inject fluids into a patient. Syringes can be connected to needles, catheters, or simply used to administer oral medicines in fluid form. In some medical imaging procedures, syringes can be used to inject radiographically opaque contrast medium (also commonly referred to as contrast agents) into a patient's vascular system. For example, angiography is a medical imaging technique used to visualize the inside of blood vessels and organs of the body. In angiography, the contrast agent is injected into the vascular system through a catheter positioned near the area of interest within the patient's body. The contrast agent is added to the blood to make the vessels visible on the x-ray images taken once the contrast agent is administered.

The contrast agent is normally injected from a manually-operated syringe into an attached medical manifold, which provides fluidic connections to a catheter, contrast agent supply, and often a saline solution supply. Connections between the manifold, syringe and catheter are typically made with a threaded connector, typically a Luer Taper connector.

For coronary angiography, it is common for between six (6) and twelve (12) milliliters of contrast agent to be injected per angiogram image. Injection of the contrast agent should be done quickly, usually within 2 seconds, in order to ensure the proper density of contrast agent in the vessels for imagining. Each angiographic procedure typically involves multiple images, which require multiple injections of contract agent.

Operators injecting the contrast agent typically use syringe made of plastic, with ring handles on the barrel (or flanges) and a plunger actuated by the operator's thumb. Often, the plunger will have a ring on the end allowing forward and backward motion with only the operator's thumb. This type of syringe provides little mechanical assistance in delivery of the contrast agent through catheters, especially given the trend towards smaller and smaller catheter diameters.

Catheter diameter is often indicated in "French" size increments, which represent intervals of 0.3 millimeters. For example, a 6 French catheter has a nominal outside diameter of 2.0 millimeters, and a 7 French catheter has a nominal outside diameter of 2.3 millimeters. Inside diameters depend on the type of catheter. Catheters used for angiography are typically diagnostic catheters, with a 5 French diagnostic catheter having an inside diameter of 1.3 millimeters.

Smaller catheters have been introduced because of the benefits associated with a smaller puncture hole required to insert the catheters into the body; as the size of the puncture hole decreases, the risk of puncture site complications and the time required for the patient to recover decreases. These recently-introduced smaller diagnostic catheters, in 4 French and 5 French sizes, have narrower diameters; a 4 French catheter can be expected to have an inside diameter of approximately 1.1 millimeters and a 5 French catheter an inside diameter of approximately 1.2 millimeters. The inside diameter of a 4 French catheter can therefore be about 15% smaller than that of a 6 French catheter and about 30% smaller than that of a 7 French catheter.

OVERVIEW

The present inventor has recognized, among other things, that the smaller inside diameters of the 4 French and 5 French catheters make manual injection of the viscous dye more difficult compared with larger catheters. This difficulty is caused by the increased amount of injection force required to propel the dye through a smaller lumen diameter to approximate the same density of dye in the blood flow as is normally achieved with larger-diameter catheters. The degree of difficulty in maintaining a minimum density of dye in the blood flow has always been a challenge, but as lumen sizes decrease, operator hand strength becomes a limiting factor in the proper administration of dye, even when two hands are used to inject. Where the operator's hand strength is not sufficient, for example after repeated injections, lower quality angiograms result and the operator's wrist, hand and fingers become fatigued. This in turn reduces the adoption rate of the smaller diagnostic catheters, delaying realization of the benefits of lower complication risk and earlier post-procedure ambulation.

The present inventor has also recognized, among other things, that traditional approaches to delivering medical fluids, such as contrast agents, at high pressure with a standard syringe poses challenges for the person administering the fluids. As discussed above, smaller diameter catheters used for medical imaging procedures present a motivation to deliver medical fluids as higher pressures. While various mechanical devices have been created to automatically deliver medical fluids at elevated pressures, these devices lack the control of a manually operated syringe and tend to be very expensive. The present syringe addresses a standard syringe's limited ability to assist in delivering medical fluids at higher pressures, among other things.

Example 1 includes a syringe comprising a housing, a shaft, a piston, a cap assembly, a bias member, and a user-actuatable locking member. The housing includes a distal end and a proximal end, with the distal end configured to interface with a patient delivery apparatus, and an internal cavity formed by an inside surface of the housing and the distal end. The shaft that includes a distal end and a proximal end, with the distal end of the shaft configured to be inserted into the housing. The piston has a peripheral sealing surface and is connected to the distal end of the shaft. The piston is also configured to be inserted into the syringe housing through the proximal end of the housing, with the peripheral sealing surface slidably engaging the inside surface of the housing to form a movable seal. The cap assembly, including a base cap engaging the shaft, is located at the proximal end of the syringe's housing. The base cap is configured to secure the piston within the housing. The bias member, with a distal end coupled to the piston and a proximal end restrained proximate to the proximal end of the syringe housing, is also included. The bias member is configured to assist in pressurizing the internal cavity of the syringe. The user-actuatable locking member is configured to user-selectively engage the shaft to inhibit unwanted movement of the shaft when engaged.

In Example 2, the syringe of Example 1 optionally includes the locking member configured to make radial contact with a radial portion of the shaft.

In Example 3, the syringe of one or any combination of Examples 1-2 optionally includes a locking member that is spring loaded for automatic engagement with the shaft.

In Example 4, the syringe of one or any combination of Examples 1-3 optionally include, a locking member that is configured to ratchet in relationship to the shaft, allowing extension of the shaft and compression of the bias member while preventing the shaft from retracting.

In Example 5, the syringe of one or any combination of Examples 1-4 optionally include, a proximal end of the housing that includes a peripheral flange and a cap assembly that includes a locking ring configured to engage the peripheral flange on the proximal end of the barrel.

In Example 6, the syringe of one or any combination of Examples 1-5 optionally includes a base cap that is a stepped cylinder with a larger diameter portion on the proximal end oriented towards the proximal end of the shaft. The cap assembly in Example 6 includes a double ring handle portion with a distal and proximal end, the distal end of the double ring handle engaging the locking ring. The cap assembly also includes a tension spring enclosed by the double ring handle, with the tension spring encircling the base cap with the proximal end of the tension spring coupled to the stepped cylinder and the distal end of the tension spring coupled to the double ring handle portion. The locking member of Example 6 includes a beveled edge on an outboard end of the locking member, and the double ring handle includes a beveled peripheral portion on the inside edge of the proximal end of the double ring handle configured to slidably engage the locking member when pressure is applied to the double ring handle towards the proximal end of the housing.

In Example 7, the syringe of one or any combination of Examples 1-6 optionally include, a shaft that is threaded, and the syringe includes a manual stop ring threaded on the threaded shaft between the cap assembly and the proximal end of the threaded shaft, with the manual stop configured to engage the cap assembly to limit retraction of the threaded shaft into the housing.

In Example 8, the syringe of Examples 7 optionally includes, a threaded shaft that includes graduation marks correlated to the amount of liquid injected, and wherein setting the manual stop ring at a particular graduation mark limits the amount of liquid ejected from the syringe to the amount indicated by the particular graduation mark.

Example 9 includes a method of expelling a liquid from a syringe. The method includes extending a shaft coupled to a piston, away from the distal end of the syringe housing, to fill an internal cavity of the syringe housing with the liquid and to store energy into a bias member coupled to the piston. The method also includes engaging a locking member to inhibit the release of energy stored in the bias member and inhibit uncontrolled ejection of liquid from the syringe. The method of Example 9 further includes releasing the energy stored in the bias member against the piston by selectively disengaging the locking member. The method of Example 9 also includes manually exerting pressure on the proximal end of the shaft to pressurize the liquid within the syringe housing while pushing the piston towards the distal end of the syringe and expelling the liquid from the distal end of the syringe.

In Example 10, the method of Example 1 optionally includes releasing the energy stored in the bias member to assist in creating higher pressurization within the syringe housing than a given pressure exerted manually on the proximal end of the shaft alone creates.

In Example 11, the method of one or any combination of Examples 9-10 optionally includes releasing the energy stored in the bias member to assist in creating a higher pressurization within the syringe housing than the manual exerting of pressure on the proximal end of the shaft alone is capable of creating.

In Example 12, the method of one or any combination of Examples 9-11, wherein the engaging the locking member occurs automatically as the shaft is retracted away from the distal end of the syringe, automatically inhibiting uncontrolled ejection of liquid due to the release of energy stored in the bias member.

In Example 13, the method of one or any combination of Examples 9-12, wherein the releasing the energy stored in the bias member occurs when proximal pressure is applied to a handle coupled to the syringe housing selectively disengaging the locking member.

In Example 14, the method of one or any combination of Examples 9-13 optionally includes setting a manual stop ring on the shaft at a position corresponding to an amount of liquid to expel, and wherein the expelling the liquid includes retracting the shaft into the syringe housing until the manual stop ring engages the syringe housing to stop further retraction of the shaft.

Example 15 includes an apparatus comprising a housing, a plunger, a bias member, and a user-actuatable locking member. The housing includes a hollow interior cavity, a distal end, and a proximal end, with the distal end configured to interface with a medical device and including an opening into the hollow interior cavity. The plunger includes a shaft and a piston at the distal end of the shaft, with the piston including a peripheral sealing surface configured to slidably engage an inside surface of the hollow interior cavity of the housing to form a movable seal, with the shaft extending beyond the proximal end of the housing. The bias member has a distal end coupled to the plunger and a proximal end restrained proximate to the proximal end of the housing, with the bias member configured to assist the plunger in pressurizing the hollow interior cavity of the housing. The user-actuatable locking member is configured to user-selectively inhibit unwanted movement of the plunger when engaged.

In Example 16, the apparatus of claim 15, wherein the shaft of the plunger is threaded, and wherein the locking member is configured to engage the threaded portion of the shaft to inhibit unwanted movement of the plunger.

In Example 17, the apparatus of one or any combination of Examples 15-16 optionally includes a handle assembly comprising a base cap and a handle portion. The base cap, coupled to the proximal end of the housing, is configured to slidably engage the shaft of the plunger and contain the locking member. The handle portion proximate to the base cap is configured to provide a leverage point to assist a user in applying pressure to the plunger.

In Example 18, the apparatus of Example 17, wherein the handle portion is slidably coupled to the base cap and configured to disengage the locking member when proximal pressure is applied to the handle portion.

In Example 19, the apparatus of one or any combination of Examples 17-18, wherein the handle portion includes a ring handle positioned on each side of the housing to form a double ring handle.

In Example 20, the apparatus of one or any combination of Examples 15-19, wherein the plunger includes a manual stop ring coupled to the plunger shaft, with the manual stop ring configured to limit retraction of the plunger into the housing.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
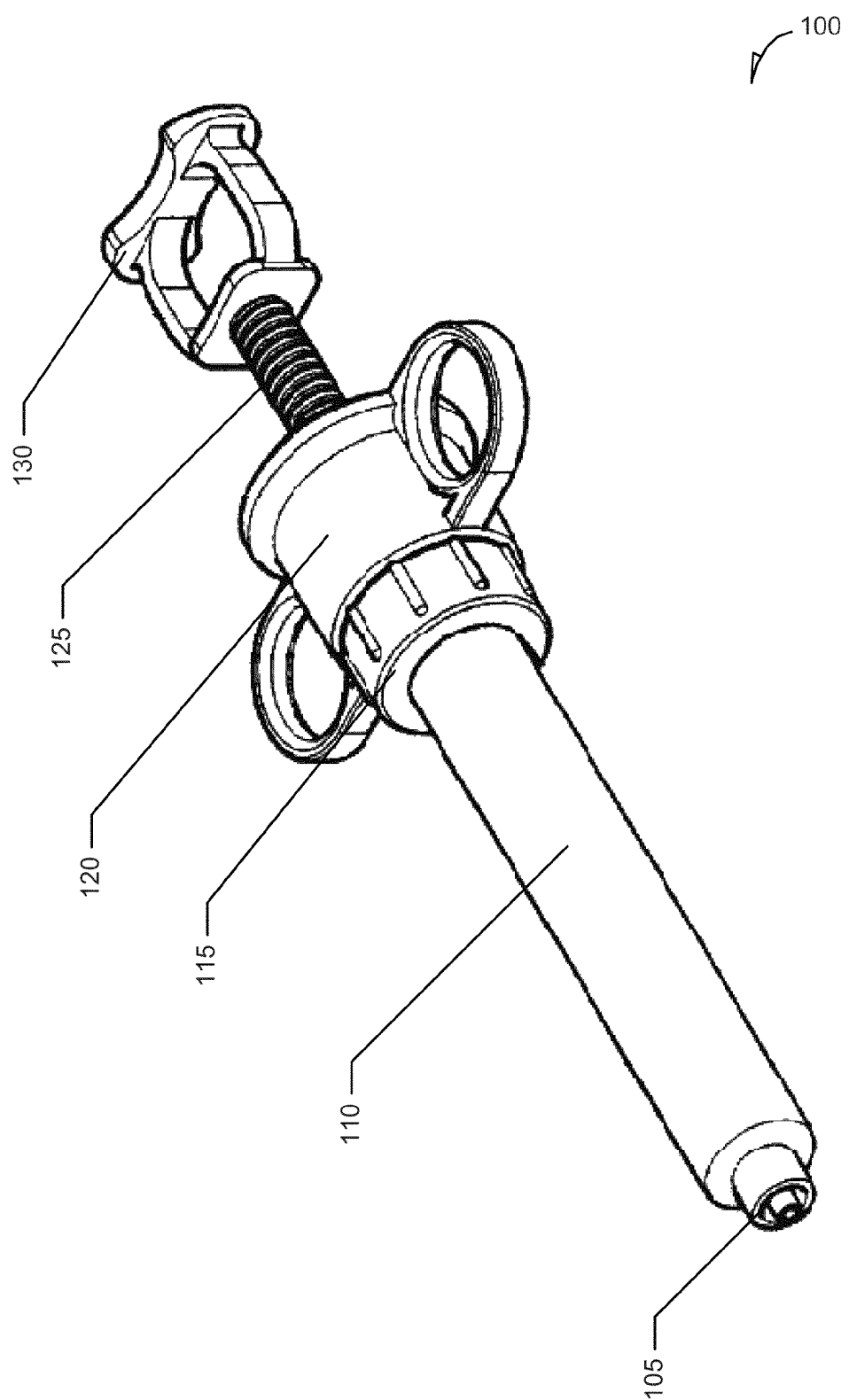
FIG. 1 is an isometric projection of an example syringe configured to deliver fluids through a patient delivery apparatus assisted by a bias member.

As described above, some medical procedures, such as angiography, require injecting fluid into a patient through a catheter or similar device. In some procedures, especially ones that benefit from the use of small diameter catheters, the pressure at which the fluid must be delivered is difficult to achieve through the use of a standard syringe. The following locking syringe with an integrated bias member addresses the difficulty in administering fluids through small diameter catheters, among other things.

Using the present locking syringe can begin from a starting position where the syringe is empty of fluid (e.g., contrast agent for angiography). The operator can pull on the ring attached to the spiral threaded plunger shaft to draw contrast into the syringe. As the plunger shaft is extended out of the syringe barrel, a locking mechanism can engage the threaded shaft such as to inhibit or prevent unwanted retraction of the shaft back into the syringe barrel. The locking mechanism (also referred to as a locking member) can be used to control unwanted release of the energy loaded into a spring or other bias member integrated into the plunger assembly as the plunger shaft is extended out of the syringe barrel. The spring can be integrated into the syringe to provide a force to assist the user in injecting fluids, such as contrast agent, through small diameter catheters. The automatic engagement of the locking mechanism prevents unintended release of the plunger, which could result in unintended release of fluid.

Once the operator has drawn the desired amount of contrast agent into the barrel of the syringe, the plunger shaft can be locked into place by the locking mechanism. This can allow the operator to manipulate another component (e.g., a manifold) or attend to one or more other operations such as to prepare the patient for the procedure. The contrast can then be injected into the patient delivery apparatus, generally through the manifold and a catheter system. In an example, the locking syringe can be operated by placing two fingers through the ring handle located at the proximalproximal end of the syringe barrel and the thumb through the ring at the proximalproximal end of the plunger shaft. Putting pressure on the double ring handle by attempting to compress the plunger back into the syringe barrel automatically disengages the locking mechanism. This can allow the plunger to move freely into the syringe and thereby expel the contrast agent previously loaded into the syringe.

With the locking mechanism released, the compressed spring is able to exert additional bias force or pressure on the plunger. This can help the operator to inject the contrast agent. As discussed above, when using small diameter catheters, the pressure required to properly administer the contrast agent can exceed the physical capabilities of the operator. The higher pressure developed with the assistance of the spring mechanism can allow the operator to deliver a desired even flow of contrast agent, thereby improving the angiogram's image quality and potentially avoiding the need to repeat a costly procedure.

During some angiography procedures, multiple images can be taken, which can involve multiple injections of contrast agent. It can be desirable to control the amount of contrast agent injected with each injection, but also desirable to only fill the syringe once before beginning the imaging procedure. To help with these needs, the present syringe can include an optional feature for setting the amount of contrast agent administered by each injection. For example, the threaded shaft of the syringe can include a small manual stop ring, which can be moved up and down the shaft such as by spinning the stop ring along the track of spiral threads.

In an example, the stop ring can be used as a manual stop such as to limit the amount of fluid injected with any individual injecting operation of the syringe. In an example, the plunger shaft can include graduations that correspond to the amount of fluid in the syringe, such as to allow the operator to set the stop ring to a specific fluid amount to be injected. In some examples, the syringe barrel can be sized to allow for enough contrast agent to be drawn into the syringe to provide enough contrast agent for multiple images without refilling. For example, the syringe barrel can be configured to hold 60 cc of contrast agent (for example, if each image requires 10 cc of contrast agent, then 6 images can be taken without the need to refill). In this example, the stop ring can be used to precisely meter 10 cc of contrast agent for each injection, simply by resetting the stop ring to the next 10 cc mark after each injection.

SYRINGE EXAMPLES

FIG. 1 is an isometric projection of an example of a syringe configured to deliver fluid, such as through a patient delivery apparatus, assisted by a bias member. The syringe 100 can include a distal end 105, a housing 110, a cap assembly 120, and a plunger 130. The cap assembly 120 optionally includes a locking ring 115. The distal end 105 of the syringe 100 can include a connector adapted to connect to one or various patient delivery apparatuses, such as a medical manifold or catheter. The connector on the distal end 105 can be a Luer taper type that provides screw-on connection to a patient delivery apparatus. If a Luer taper type connector is included on the distal end 105, the connector can conform to ISO 594:1986 "Conical fittings with a 6% (Luer) taper for syringes, needles and certain other medical equipment."

In an example, the housing 110 is barrel shaped and can be made of clear or translucent plastic or other suitable medical grade material. In another example, the housing 110 can be square in cross-sectional shape. In yet another example, the housing 110 can be a hexagon or some other symmetric geometrical cross-sectional shape. The housing 110 forms an inner cavity that is adapted to hold a medical fluid such as for injection into a patient. In certain examples, the housing 110 is made of clear material and includes graduation marks that indicate the amount of fluid drawn into the syringe. The graduation marks correspond to the cavity volume created by the inner surface of the housing 110, the distal end 105, and a piston attached to the plunger 130. As the plunger is drawn out of the housing 110, the inner cavity space is expanded in volume corresponding to the graduation marks.

The cap assembly 120 can include a set of ring handles (such as shown in FIG. 1) or, additionally or alternatively, a set of flanges. The rings or flanges can provide a location for the operator to place his or her fingers such as to manipulate the plunger while controlling the syringe 100. The cap assembly 120 can include a locking ring 115, which can be used to hold the cap assembly 120 in place on the proximal end of the housing 110. In certain examples, such as shown in detail in FIG. 2, the cap assembly can be an active component of the syringe 100. In other examples, the cap assembly can be an essentially static component of the syringe 100. In an example, the cap assembly 120 and ring handle or flanges can be molded into the housing 110.

The plunger 130 can include a proximal end, a shaft 125, and a piston (not shown in FIG. 1). The proximal end of the plunger 130 can include a single ring such as to assist in extracting the plunger 130 from the housing 110. In another example, the proximal end of the plunger 130 can include a flat surface such as suitable for exerting pressure to eject fluid out of the syringe 100. The shaft 125 can include a threaded cylindrical shaft, a smooth cylindrical shaft, or some other suitable configuration. In an example in which the shaft 125 is threaded, the shaft 125 can be made from a plastic polymer or a medical grade metal, such as stainless steel. Table 1 includes a listing of material used in an example embodiment:

TABLE 1

Example Syringe Materials List

| | |
|---|---|
| Housing 110 | PC (Polycarbonate) |
| Piston 210 | Silicone rubber |
| Peripheral sealing surface 212 | Silicone rubber |
| shaft 125 | POM □Polyoxymethylene) |
| locking ring 115 | ABS (acrylonitrile butadiene styrene) |
| base cap 230 | ABS (acrylonitrile butadiene styrene) |
| double ring handle 220 | ABS (acrylonitrile butadiene styrene) |
| Cap assembly 120 | ABS (acrylonitrile butadiene styrene) |
| locking member 240 | PC (Polycarbonate) |
| engagement spring 245 | Stainless Steel Spring Wire (0.6 mm) |
| tension spring 225 | Stainless Steel Spring Wire (1.2 mm) |
| Bias member 215 | Stainless Steel Spring Wire (1.5 mm) |

Figure 2:
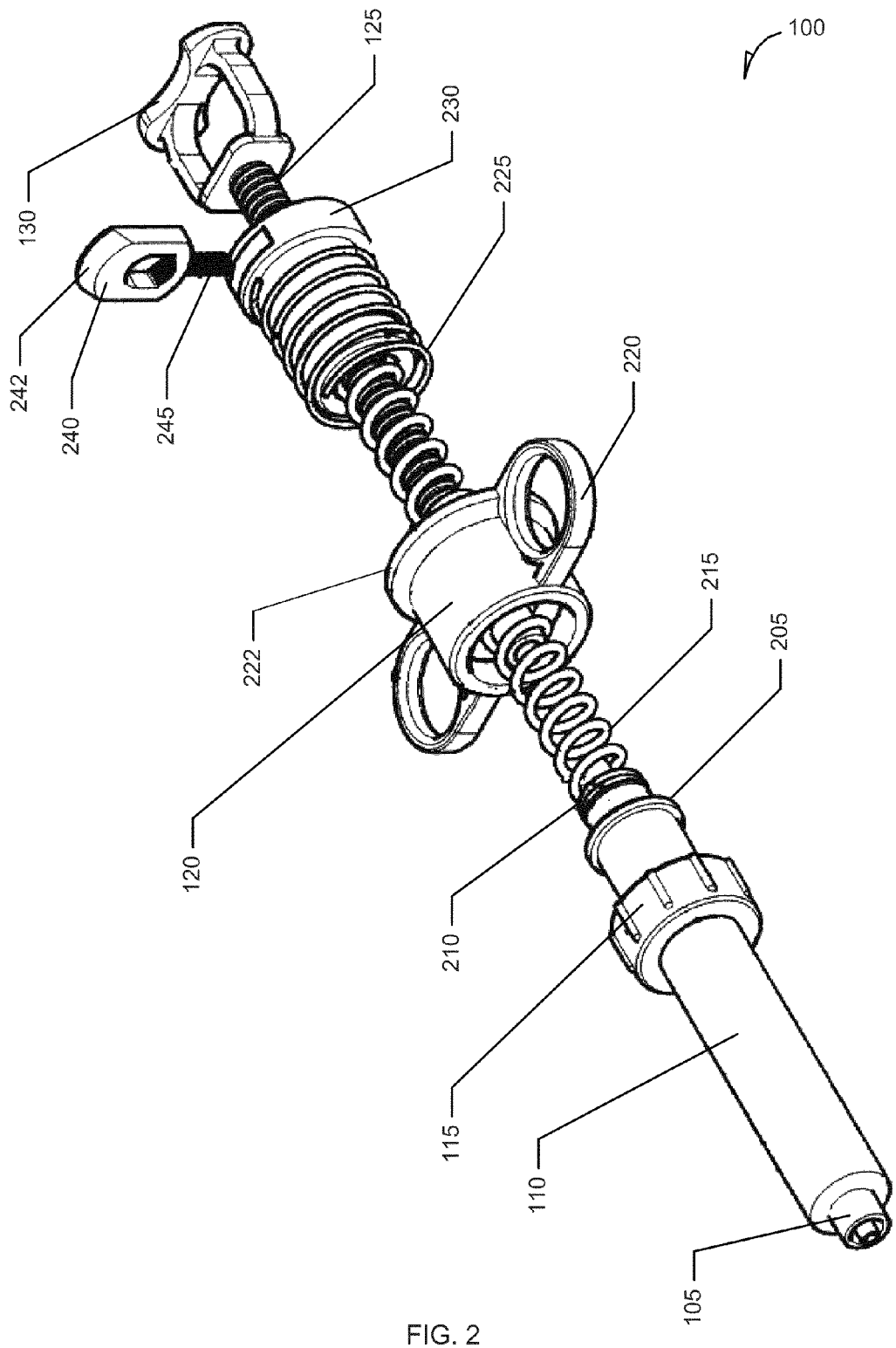
FIG. 2 is an exploded isometric projection of an example syringe capable of delivering fluids through a patient delivery apparatus assisted by a bias member.

FIG. 2 is an exploded isometric projection of an example of a syringe capable of delivering a fluid, such as through a patient delivery apparatus, assisted by a bias member. The syringe 100 depicted in the example of FIG. 2 can include a distal end 105, a housing 110, a cap assembly 120, a plunger 130, a piston 210, a bias member 215, and a locking member 240. In an example, the housing 110 can include a flange 205 such as located near the proximal end of the housing 110. The cap assembly 120 can include a locking ring 115, a double ring handle 220, a tension spring 225, and a base cap 230. The locking member 240 can include an engagement spring 245.

In an example, the plunger 130 can includes a shaft 125 with a piston 210 attached to the distal end of the shaft 125. The shaft 125 can be threaded or smooth, such as depending upon how the locking member 240 is configured. The piston 210 can be configured to slidably engage the interior surface of the housing 110 such as to create a fluid-tight seal.

In an example, the housing 110 can include a flange 205 near the proximal end of the housing 110 such as for engaging the locking ring 115 portion of the cap assembly 120. The flange 205 can extend enough from the periphery of the housing 110 to allow the inside portion of the locking ring 115 to engage the flange 205. In certain examples, the locking ring 115 can snap over the flange 205 such as to secure the cap assembly 120. In an example, the locking ring 115 can include a threaded portion adapted to engage the flange 205 such as to secure the cap assembly 120. In an example, the locking ring 115 can include an interior surface that can abut the distal side of the flange 205, while also including a threaded portion to attach to a portion of the cap assembly 120.

In an example, the cap assembly 120 can include a base cap 230 that can slide into the double ring handle 220 portion and can thread into the locking ring 115. Threading the base cap 230 into the locking ring 115 can provide a structure to secure the proximal end of the bias member 215 and to allow the distal end of the bias member 215 to exert a force on the piston 210 portion of the plunger 130. In certain examples, the locking ring 115 can snap onto a groove in the base cap 230. In certain examples, the locking ring 115 can snap over a flange on the distal end of the base cap 230. The base cap 230 can be surrounded by a tension spring 225 that can provide resistance to sliding movement of the double ring handle 220. The base cap 230 can also contain the locking member 240 and engagement spring 245. In this configuration, the base cap 230 can allow small movements of the double ring handle 220 along the axial direction of the housing 110. The double ring handle 220 can engage and disengage the locking member 240 while sliding over the base cap 230. In certain examples, a chamfered or beveled inner surface 222 of the double ring handle 220 can engage a chamfered or beveled outer or outbound surface 242 of the locking member 240 such as to disengage the locking member 240 from the threaded shaft 125. In this configuration, the tension spring 225 can be used to prevent unintended disengagement of the locking member 240.

In an example, the plunger 130 can include a single ring handle on the proximal end of a threaded shaft 125 with the piston 210 connected to the distal end of the shaft 125. The piston 210 can include a peripheral sealing surface such as to create a slidable seal when inserted into the housing 110. In this example, the plunger shaft 125 can be wrapped with a bias member 215 that can be configured to provide a force against the piston 210 when loaded with energy. The bias member 215 can be loaded with energy by extracting the plunger 130 from the housing 110 (moving the ring handle in a proximal direction away from the housing 110). In an example, the bias member 215 can include a coil spring.

In an example, the locking member 240 can automatically engage the threaded portion of the shaft 125 as the plunger 130 is extended out of the housing 110. In this configuration, the locking member 240 can automatically engage the shaft 125 such as to prevent the unwanted unloading of the energy being stored in the bias member 215 as the plunger 130 is extended. The engagement spring 245 can provide a force against the locking member 240 such as to engage the threaded shaft 125, thereby locking the shaft 125 into place. The locking member 240 can include engagement teeth that can be configured to allow the locking member to automatically ratchet as the shaft 125 is extended. In an example, the ratcheting action allows the shaft 125 to be extended, but does not allow any return movement without manually disengaging the locking member 240. Further details regarding an example of the operation of the locking member 240 are provided below in reference to FIG. 4.

Figure 3:
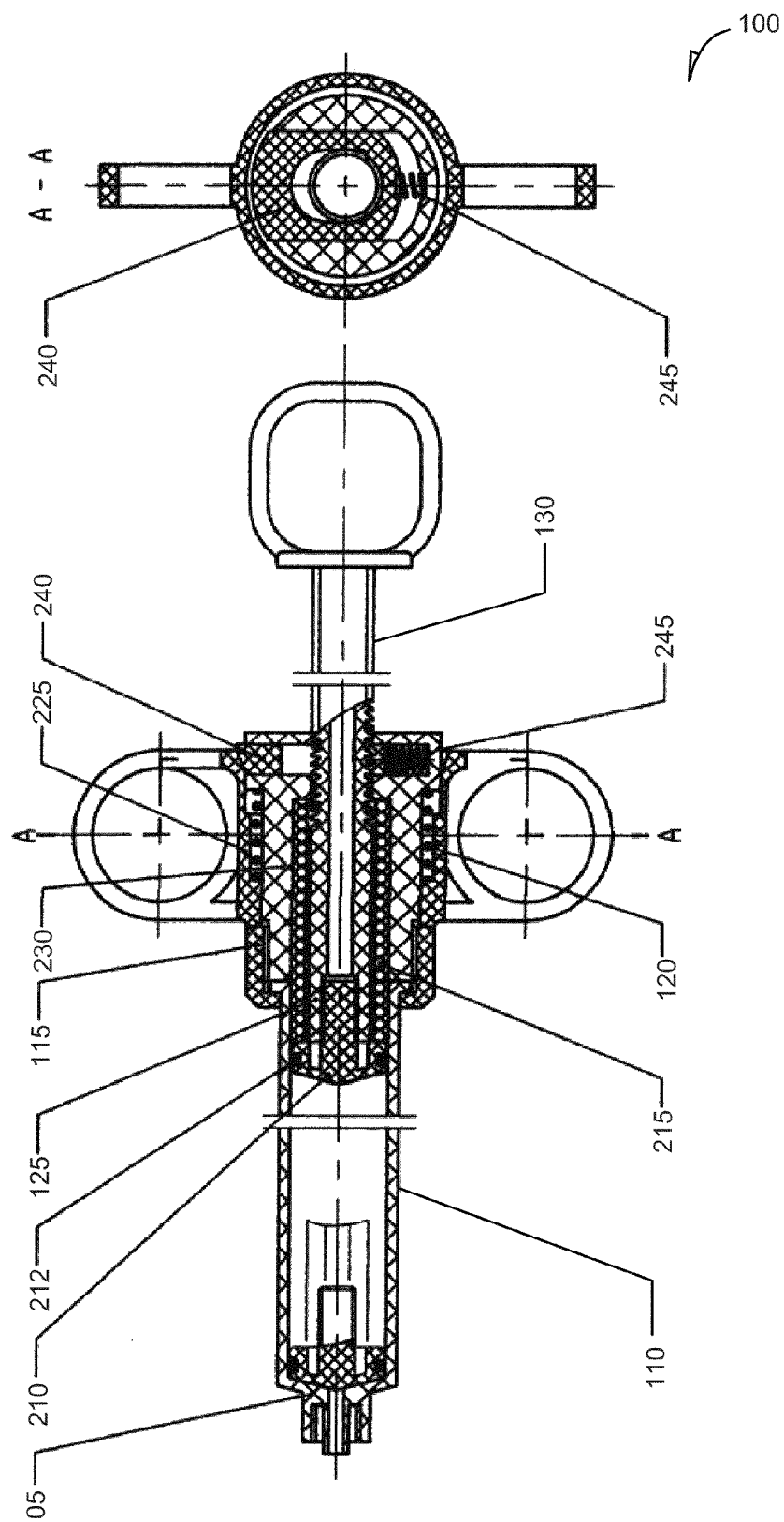
FIG. 3 is a cutaway drawing of an example syringe capable of delivering fluids through a patient delivery apparatus assisted by a bias member.

FIG. 3 is a cutaway drawing of an example of a syringe capable of delivering fluids through a patient delivery apparatus assisted by a bias member. The cutaway drawing of syringe 100 illustrates an example of the piston's 210 peripheral sealing surface 212, as well as showing assembled locations of components such as the bias member 215, the tension spring 225, the locking member 240, and the engagement spring 245. FIG. 3 illustrates an example of the bias member 215 in a compressed (e.g., loaded with potential energy) position with the plunger 130 extended out of the housing 110. FIG. 3 also depicts a cutaway view of an example of the distal end 105, the locking ring 115, the cap assembly 120, the shaft 125, and the base cap 230. The section A-A depicts an example of a method of engaging the shaft with the locking member 240. The section A-A also depicts an example of a position for the engagement spring 245.

In certain examples, the piston's 210 peripheral sealing surface 212 can include a rubber O-ring. In an example, the piston 210 can be molded from rubber or a flexible plastic material and the sealing surface 212 can include a molded portion of the piston 210. In certain examples, the sealing surface 212 can include a circular gasket, such as made from rubber of some similar polymer material with a profile adapted for sealing against the inner surface of the housing 110.

Figure 4:
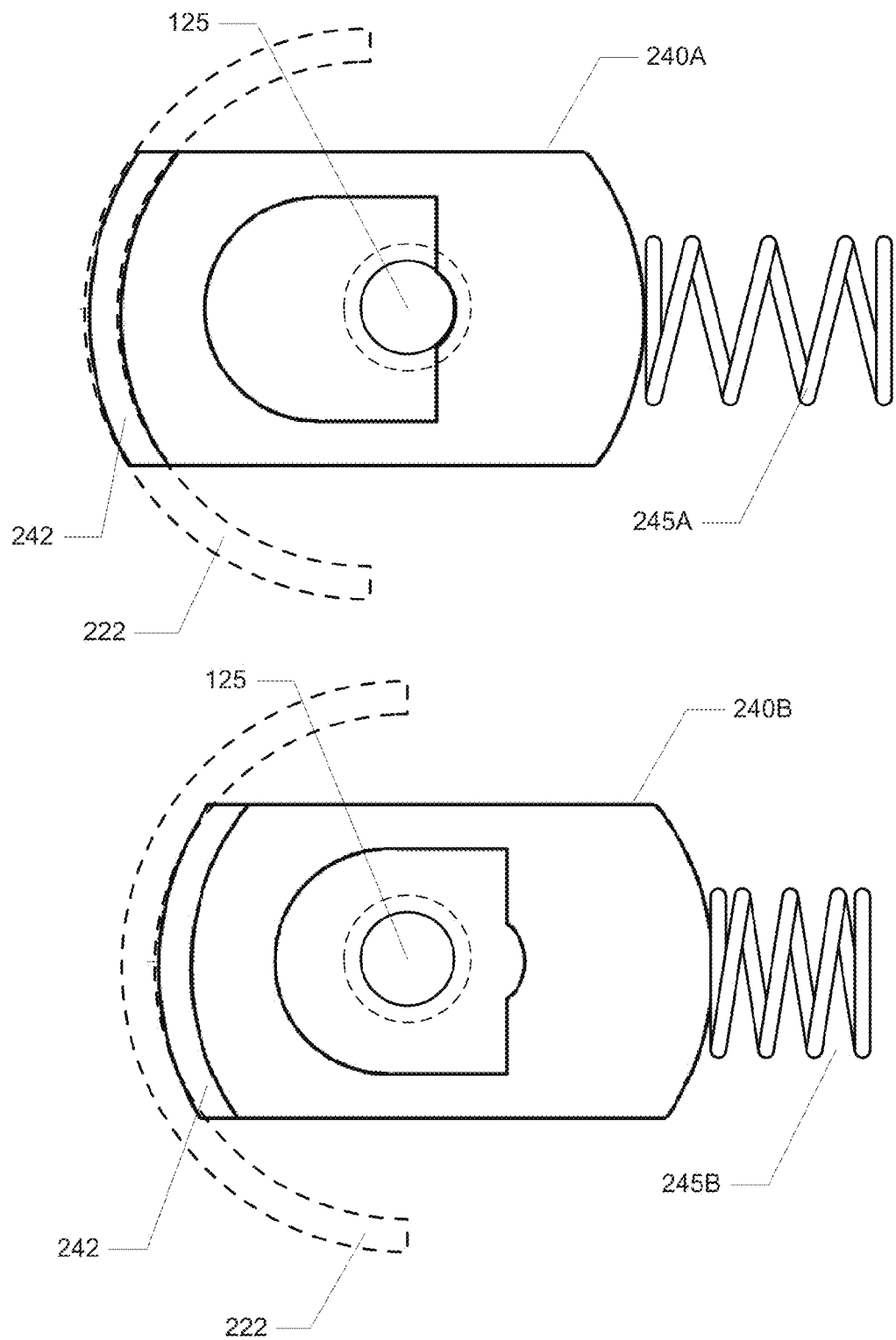
FIG. 4 is a detailed drawing of a user-actuatable locking mechanism for a bias member assisted syringe, according to an example embodiment.

FIG. 4 is a detailed drawing of an example of a user-actuatable locking mechanism for an example of the present bias-member-assisted syringe. FIG. 4 includes illustrations of the locking member 240A, 240B, engagement spring 245A, 245B, and the plunger shaft 125 in two different positions (e.g., locked and unlocked). Locking member 240A and engagement spring 245A depict an example of the locking member 245 engaged with the shaft 125. In this example, the locking member 240 includes teeth configured to mate with the thread pattern on shaft 125. The mating teeth can also be configured to, in conjunction with the engagement spring, allow for a one-way ratcheting movement of the shaft 125, as discussed above. In this example, the chamfered outer edge 242 of the locking member 240A is not engaged by the chamfered edge 222 of the double ring handle 220.

In the second example depicted in FIG. 4, the locking member 240B and engagement spring 245B are disengaged from the shaft 125, such as for allowing the shaft to move as directed by the operator and bias member 215. In this second example of position, the chamfered outer edge 242 of locking member 240 can be engaged with the chamfered inner edge 222 of the double ring handle 220. In an example, the chamfered edges 222, 242 can be engaged such as by applying proximal pressure on the double ring handle 220. The engagement of the two chaffered surfaces can cause the engagement spring 245B to be compressed as the locking member 240B disengages the shaft 125. Releasing the pressure applied on the double ring handle 220 can allow the locking member 240B to return to the engaged position depicted by locking member 240A. In this example, the chamfered edge 222 of the double ring handle 220 depicted in FIG. 4 is only partially shown for illustrative purposes. All the components depicted in FIG. 4 are not necessarily drawn to scale such as with respect to each other.

METHOD OF USE EXAMPLES

Figure 5:
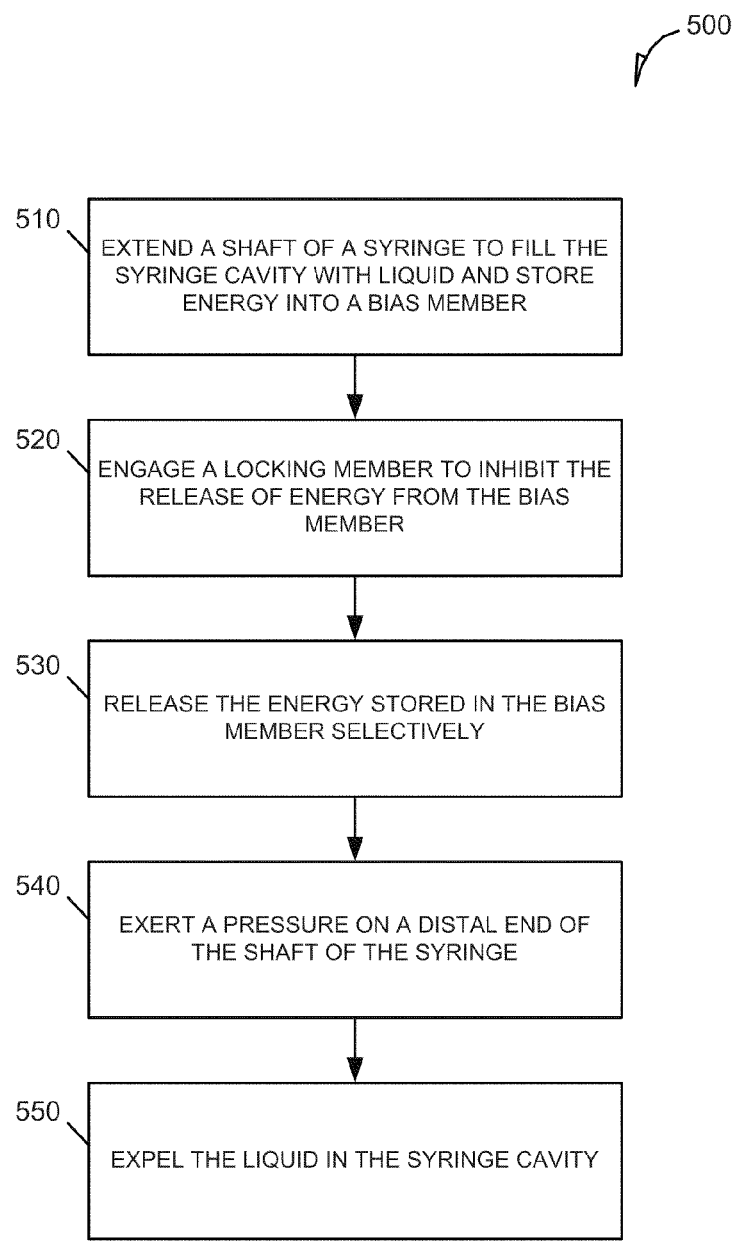
FIG. 5 is a flowchart illustrating an example method of using a bias member assisted locking syringe.

FIG. 5 is a flowchart illustrating an example of a method of using a bias-member-assisted locking syringe. In an example, a method 500 can include, at 510, extending a shaft of a syringe to fill the syringe cavity with liquid and to store energy into a bias member. At 520, the method 500 can include engaging a locking member to inhibit the release of energy from the bias member. At 530, the method 500 can include selectively releasing the energy stored in the bias member. At 540, the method 500 can include exerting a pressure on a proximal end of the shaft of the syringe. At 550, the method 500 can include expelling the liquid in the syringe.

At 510, in an example, an operator can extend the shaft 125 of the syringe 100 to fill the inner cavity of the housing 110 with liquid and to store energy into the bias member 215. Optionally, the method 500 can include an operation before 510 where the operator can connect the syringe 100 to a source of the contrast agent or other liquid. In an example, the syringe 100 can also be connected to a medical manifold system such as for providing connections to multiple fluid sources or to the patient delivery apparatus. In certain examples, extending the shaft 125 can include manually disengaging the locking member 240. In certain examples, extending the shaft 125 at 510 can include the locking member 240 automatically ratcheting as the shaft 125 extends.

At 520, the method 500 can continue such as with the locking member 240 engaging the shaft 125 such as to inhibit the release of energy from the bias member 215. Locking the shaft 125 can also inhibit or prevent unwanted ejection of liquid from the syringe 100. Operation 520 can occur automatically such as through the ratcheting action of locking member 240, as described above. In an example, the locking member 240 can be configured to allow for manual engagement and disengagement.

The method 500 can continue with operations 530 and 540, which can occur in parallel, e.g., concurrently. In an example, the operator can release the energy stored in the bias member 215 and exert a pressure on the proximal end of the shaft 125 of the syringe 100 concurrently. In an example, the syringe 100 can be configured so that the double ring handle 220 can selectively disengage the locking member 240 such as by squeezing the double ring handle 220 while putting pressure on the proximal end of the shaft 125. Disengaging the locking member 240 can release the energy stored in the bias member 215, thereby assisting the operator in injecting the liquid into a patient delivery apparatus at 550.

In an example, the method 500 can continue at 530 with the operator selectively releasing the energy stored in the bias member and then, at 540, with the operator exerting pressure on the proximal end of the shaft 125 of the syringe 100. Operations 530 and 540 can lead to operation 550 in which the liquid can be expelled from the syringe 100 through the distal end 105.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
   a housing including a hollow interior cavity, a distal end, and a proximal end, the distal end configured to interface with a medical device and including an opening into the hollow interior cavity, the proximal end including a peripheral flange;
   a plunger including a shaft and a piston at a distal end of the shaft, the piston including a peripheral sealing surface configured to slidably engage an inside surface of the hollow interior cavity of the housing to form a movable seal, the shaft extending beyond the proximal end of the housing;
   a bias member with a distal end coupled to the plunger and a proximal end restrained proximate to the proximal end of the housing, the bias member configured to assist the plunger in pressurizing the hollow interior cavity of the housing;
   a cap assembly including,
      a base cap engaging the shaft and located at the proximal end of the housing, the base cap configured to secure the piston within the housing,
      a locking ring to engage the peripheral flange,
      a double ring handle portion with a distal end engaging the locking ring, and
      a tension spring disposed between the double ring handle and a portion of the base cap;
   a user-actuatable locking member embedded within the double ring handle and spring loaded to user-selectively inhibit unwanted movement of the plunger when engaged, the locking member including a beveled outer edge; and
   wherein the double ring handle includes a beveled peripheral portion on an inside edge of the proximal end of the double ring handle configured to slidably engage the locking member when pressure is applied to the double ring handle toward the proximal end of the housing.

2. The apparatus of claim 1, wherein the shaft of the plunger is threaded; and
   wherein the locking member is configured to engage the threaded portion of the shaft to inhibit unwanted movement of the plunger.

3. The apparatus of claim 1, wherein the base cap is coupled to the proximal end of the housing, configured to slidably engage the shaft of the plunger and contain the locking member; and
   wherein the double ring handle portion proximate to the base cap and configured to provide a leverage point to assist a user in applying pressure to the plunger.

4. The apparatus of claim 3, wherein the double ring handle portion is slidably coupled to the base cap and configured to disengage the locking member when proximal pressure is applied to the double ring handle portion.

5. The apparatus of claim 1, wherein the plunger includes a manual stop ring coupled to the plunger shaft, the manual stop ring configured to limit retraction of the plunger into the housing.

6. A syringe comprising:
   a housing including a distal end configured to interface with a patient delivery apparatus, a proximal end including a peripheral flange, and an internal cavity formed by an inside surface of the housing and the distal end;
   a shaft including a distal end and a proximal end, the distal end configured to be inserted into the housing;
   a piston including a peripheral sealing surface and connected to the distal end of the shaft, the piston configured to be inserted into the housing through the proximal end of the housing, with the peripheral sealing surface slidably engaging the inside surface of the housing to form a movable seal;
   a cap assembly including,
      a base cap engaging the shaft and located at the proximal end of the housing, the base cap configured to secure the piston within the housing,
      a locking ring to engage the peripheral flange,
      a double ring handle portion with a distal end engaging the locking ring, and
      a tension spring disposed between the double ring handle and a portion of the base cap;
   a bias member with a distal end coupled to the piston, the bias member configured to assist in pressurizing the internal cavity;
   a user-actuatable locking member spring-loaded to user-selectively engage the shaft to inhibit unwanted movement of the shaft when engaged, the locking member including a beveled outer edge; and
   wherein the double ring handle includes a beveled peripheral portion on an inside edge of the proximal end of the double ring handle configured to slidably engage the locking member when pressure is applied to the double ring handle toward the proximal end of the housing.

7. The syringe of claim 6, wherein the locking member is configured to make radial contact with a radial portion of the shaft.

8. The syringe of claim 6, wherein the locking member is configured to ratchet in relationship to the shaft, allowing extension of the shaft and compression of the bias member while inhibiting the shaft from retracting until the locking member is released.

9. The syringe of claim 6, wherein the shaft is threaded; and
   including a manual stop ring threaded on the threaded shaft between the cap assembly and the proximal end of the threaded shaft, the manual stop configured to engage the cap assembly to limit retraction of the threaded shaft into the housing.

10. The syringe of claim 9, wherein the threaded shaft includes graduation marks correlated to an amount of liquid injected; and
    wherein setting the manual stop ring at a particular graduation mark limits the amount of liquid ejected from the syringe.

* * * * *